US006974452B1

(12) United States Patent
Gille et al.

(10) Patent No.: US 6,974,452 B1
(45) Date of Patent: Dec. 13, 2005

(54) CUTTING AND CAUTERIZING SURGICAL TOOLS

(75) Inventors: Henrick K. Gille, Oceanside, CA (US); William D. Fountain, Carlsbad, CA (US); Fritz A. Brauer, Oceanside, CA (US)

(73) Assignee: Clinicon Corporation, Carisbad, CA (US)

( * ) Notice: Subject to any disclaimer, the term of this patent is extended or adjusted under 35 U.S.C. 154(b) by 0 days.

(21) Appl. No.: 09/546,097

(22) Filed: Apr. 10, 2000

Related U.S. Application Data (60) Provisional application No. 60/175,772, filed on Jan. 12, 2000.

(51) Int. Cl.$^7$ ............................................. A61B 18/12
(52) U.S. Cl. ............................. 606/37; 606/45; 606/49
(58) Field of Search ........................... 606/37–45, 167, 606/49

(56) References Cited

U.S. PATENT DOCUMENTS

| | | | |
|---|---|---|---|
| 4,161,950 A * | 7/1979 | Doss et al. ................... 219/770 |
| 4,185,632 A * | 1/1980 | Shaw ........................... 219/233 |
| 4,185,633 A | 1/1980 | Prozorov et al. |
| 4,209,017 A | 6/1980 | Shaw |
| 4,228,800 A * | 10/1980 | Degler et al. ................... 606/48 |
| 4,248,231 A * | 2/1981 | Herczog et al. ............... 606/50 |
| 4,273,127 A | 6/1981 | Auth et al. |
| 4,314,559 A * | 2/1982 | Allen ............................ 30/140 |
| 4,619,563 A | 10/1986 | Doting ......................... 407/118 |
| 4,627,435 A * | 12/1986 | Hoskin .......................... 219/233 |
| 4,640,279 A * | 2/1987 | Beard ............................ 606/28 |
| 4,651,734 A * | 3/1987 | Doss et al. ...................... 606/50 |
| 4,657,017 A * | 4/1987 | Sorochenko ................... 606/50 |
| 4,699,142 A | 10/1987 | Seal et al. ..................... 128/339 |
| 4,943,720 A | 7/1990 | Jones .......................... 250/306 |
| 5,110,577 A | 5/1992 | Tamor et al. |
| 5,125,927 A * | 6/1992 | Belanger ....................... 606/45 |
| 5,190,541 A | 3/1993 | Abele et al. ................... 606/46 |
| 5,200,609 A | 4/1993 | Sting et al. .................. 250/226 |
| 5,270,543 A | 12/1993 | Visser et al. ................. 250/306 |
| 5,278,431 A | 1/1994 | Das ............................. 257/77 |
| 5,308,311 A * | 5/1994 | Eggers et al. ................ 219/227 |
| 5,316,559 A | 5/1994 | Klievoneit et al. ........... 51/295 |
| 5,323,475 A | 6/1994 | Marsden et al. |
| 5,324,289 A * | 6/1994 | Eggers ......................... 606/48 |
| 5,330,471 A * | 7/1994 | Eggers ......................... 606/48 |
| 5,337,388 A | 8/1994 | Jacobowitz et al. |
| 5,380,321 A | 1/1995 | Yoon |
| 5,401,272 A | 3/1995 | Perkins |
| 5,413,575 A * | 5/1995 | Haenggi ....................... 606/39 |
| 5,453,293 A | 9/1995 | Beane et al. .................. 427/96 |
| 5,475,318 A | 12/1995 | Marcus et al. .............. 324/762 |
| 5,540,676 A | 7/1996 | Freiberg |
| 5,601,924 A | 2/1997 | Beane et al. ................. 428/403 |
| 5,607,435 A | 3/1997 | Sachdeva et al. |

(Continued)

FOREIGN PATENT DOCUMENTS

DE          19738512 A1    2/1999

(Continued)

*Primary Examiner*—Henry M Johnson, III
(74) *Attorney, Agent, or Firm*—Fish & Richardson P.C.

(57) ABSTRACT

A surgical tool that can be used for both cauterizing and cutting during a surgical procedure. The surgical tool may include a tip having an edge for cutting and electrodes formed at or near the edge for cauterizing. The electrodes are configured to be in electrical contact with a contact electrode passing through a handle of the surgical tool. An electrical current may be passed through the contact electrode to the electrodes formed at or near the edge of the tip.

15 Claims, 8 Drawing Sheets

U.S. PATENT DOCUMENTS

| | | | |
|---|---|---|---|
| 5,611,798 A * | 3/1997 | Eggers | 219/230 |
| 5,697,926 A | 12/1997 | Weaver | 606/41 |
| 5,763,879 A | 6/1998 | Zimmer et al. | 250/306 |
| 5,893,849 A | 4/1999 | Weaver | 606/41 |
| 5,911,719 A * | 6/1999 | Eggers | 606/29 |
| 5,925,039 A | 7/1999 | Landingham | 606/41 |
| 5,925,043 A * | 7/1999 | Kumar et al. | 29/825 |
| 5,951,543 A | 9/1999 | Brauer | 606/10 |
| 6,037,240 A | 3/2000 | Floeter et al. | |
| 6,039,735 A | 3/2000 | Greep | 606/45 |
| 6,066,137 A | 5/2000 | Greep | 606/45 |
| 6,162,219 A | 12/2000 | Nilsson et al. | |
| 6,447,511 B1 * | 9/2002 | Slater | 606/48 |
| 6,582,513 B1 | 6/2003 | Linares et al. | |

FOREIGN PATENT DOCUMENTS

| | | |
|---|---|---|
| EP | 0 227 258 | 7/1987 |
| GB | 2 071 500 A | 9/1981 |
| GB | 2 102 678 A | 2/1983 |
| WO | WO 98/02956 | 1/1998 |
| WO | WO 99/00532 | 1/1999 |
| WO | WO 99/40858 | 8/1999 |

* cited by examiner

CUTTING AND CAUTERIZING SURGICAL TOOLS

CROSS-REFERENCE TO RELATED APPLICATIONS

This application claims the benefit of U.S. Provisional Patent Application No. 60/175,772, filed Jan. 12, 2000.

BACKGROUND

The present invention relates generally to surgical tools, and more particularly, to surgical tools that can be used for cauterizing and cutting during a surgical operation.

Bleeding commonly occurs during surgical procedures. Typically, the bleeding emanates from a bleeding vessel during a cutting procedure using, for example, a scalpel. The bleeding can greatly obscure surgeon's view. To control the bleeding, the vessel can be clamped with a surgical instrument to stop the flow of blood, and the vessel can be mended. The mending, however, tends to cause infection and improper healing.

More recently, electrocautery systems have been used to control bleeding from a vessel. An electrocautery system delivers an electrical current through a cable to an electrode, which is positioned at the bleeding site. A heat or energy source is used to gradually increase the temperature of the electrode, which heats the tissue in order to heat the tissue surrounding the bleeding vessel. By heating the tissue, cauterization occurs at the point of bleeding.

Known electrocautery systems are separate and distinct from the cutting tools used during surgical procedures. This means that a surgeon must constantly switch between the cutting tool and the electrocautery system during an operation. Accordingly, this increases the risk of mistakes, makes the surgery more complex, and delays the surgical procedure.

Thus, a need exists for surgical tools that allow a surgeon to perform cutting and cauterizing at an application site in which the cutting and cauterizing can be performed with the same surgical tool.

SUMMARY

In general, the invention is directed to an apparatus for cutting and cauterizing during a surgical procedure. The apparatus includes a surgical tool having a tip with one or more edges for cutting, and at least one electrode coupled to at least a portion of the tip for cauterizing. A surgeon can thus perform cutting and cauterizing using the same surgical tool.

Accordingly, in one aspect, the invention is directed to a surgical tool having a tip with at least one mechanical cutting edge. At least one electrode is formed integral with the tip.

In another aspect, the invention is directed to a method for manufacturing a surgical tool that includes coupling a tip to a handle. The method also includes forming one cutting edge on the tip, and forming at least one electrode integral with the tip.

In another aspect, the invention is directed to a surgical tool that includes a housing and a tip formed from an electrically conductive material. A cutting edge is bonded to the tip.

In yet another aspect, the invention is directed to a surgical tool that includes a tip having a mechanical cutting edge in which the tip is coupled to a handle. A push/pull device is formed integral with the handle, and an electrode is coupled to the distal end of the push/pull device. The electrode passes across a surface of the tip, when the push/pull device is actuated.

In yet another aspect, the invention is directed to a system for cutting and cauterizing that includes a surgical tool having a tip coupled to a handle, the tip includes a mechanical cutting edge and an electrode formed integral with the tip; and an energy source coupled to the handle to deliver electrocautery energy to the tip via a contact electrode passing through the handle.

The details of one or more embodiments of the invention are set forth in the accompanying drawings and the description below. Other features, objects, and advantages of the invention will be apparent from the description and drawings, and from the claims.

DETAILED DESCRIPTION

In general, the invention is directed to an apparatus for cutting and cauterizing during a surgical procedure. The apparatus includes a surgical tool having a tip with one or more edges for cutting, and one or more electrodes formed on at least a portion of the tip for cauterizing. The cutting edge preferably has a sharpness suitable for making incisions or for cutting tissue. The electrode can be used to pass electrocautery energy to an incision site to control bleeding.

The invention is based on a principle different from known surgical tools for cauterizing and cutting that are used in industrial and medical applications. The apparatus does not use an electrode from a separate electrocautery system to cauterize an area around the incision site; rather, the apparatus includes an electrode formed on at least a portion of the tip to deliver electrocautery energy from an energy source virtually simultaneously during a cutting procedure. The cautery and cutting can thus be performed using the same surgical tool.

Unless otherwise defined, all technical and scientific terms used herein have substantially the same meaning as commonly understood by one of ordinary skill in the art to which this invention belongs. Although many methods and materials similar or equivalent to those described herein can be used in the practice or manufacturing of the present invention, suitable materials and configurations are described below.

Surgical tools for mechanical cutting can be made with tips with multiple facets to form multiple types of cutting edges. For example, the tip can be "bifacet" (FIG. 1A), or "lance or spear" (FIG. 1B).

Figure 1A:
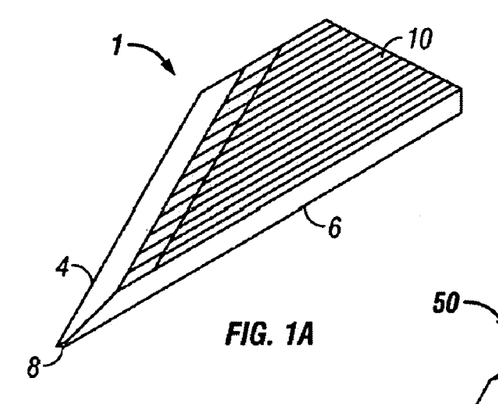
FIG. 1A illustrates a bifacet tip in a first embodiment.
Figure 1B:
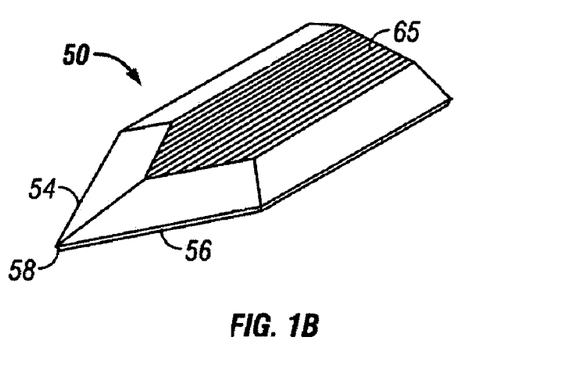
FIG. 1B illustrates a lance or spear tip in a first embodiment.

FIG. 1A shows a bifacet tip 1 with beveled edge 4 and a face 6. The edge 4 may be used for cutting during a surgical procedure. The edge 4 and the face 6 form an apex 8, which may be used for piercing. Preferably, the edge 4 has a sharpness suitable to cut tissue or make incisions.

Figure 2A:
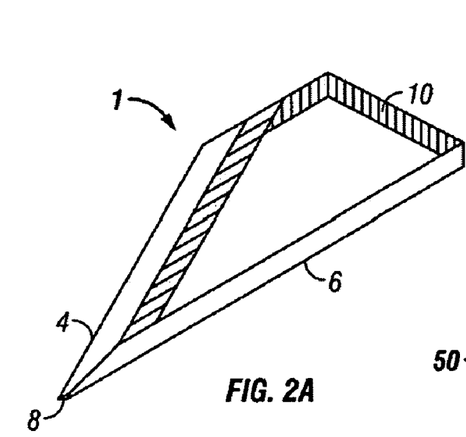
FIG. 2A illustrates the bifacet tip of FIG. 1A in a second embodiment.

A portion of the tip 1 may be covered with one or more electrodes 10. In one configuration, as shown in FIG. 1A, the electrodes 10 are formed on both sides of the tip 1 such that only the edge 4 and the face 6 are exposed. The electrodes 10 may be formed from current carrying metals, such as titanium, platinum, copper, nickel, tin, gold, chromium, iron, silver, or other similar conductive metals or alloys. The electrodes 10 may also be formed from current carrying ceramic materials, such as titanium nitride, silicon carbide, or tungsten carbide. Alternatively, as shown in FIG. 2A, the electrodes 10 may be formed on only a portion of the tip 1. The electrical conductors 10 may be applied to one or more surfaces of the tip 1 by painting, vapor deposition, chemical coating, adhesively bonding or other similar techniques.

Figure 3:
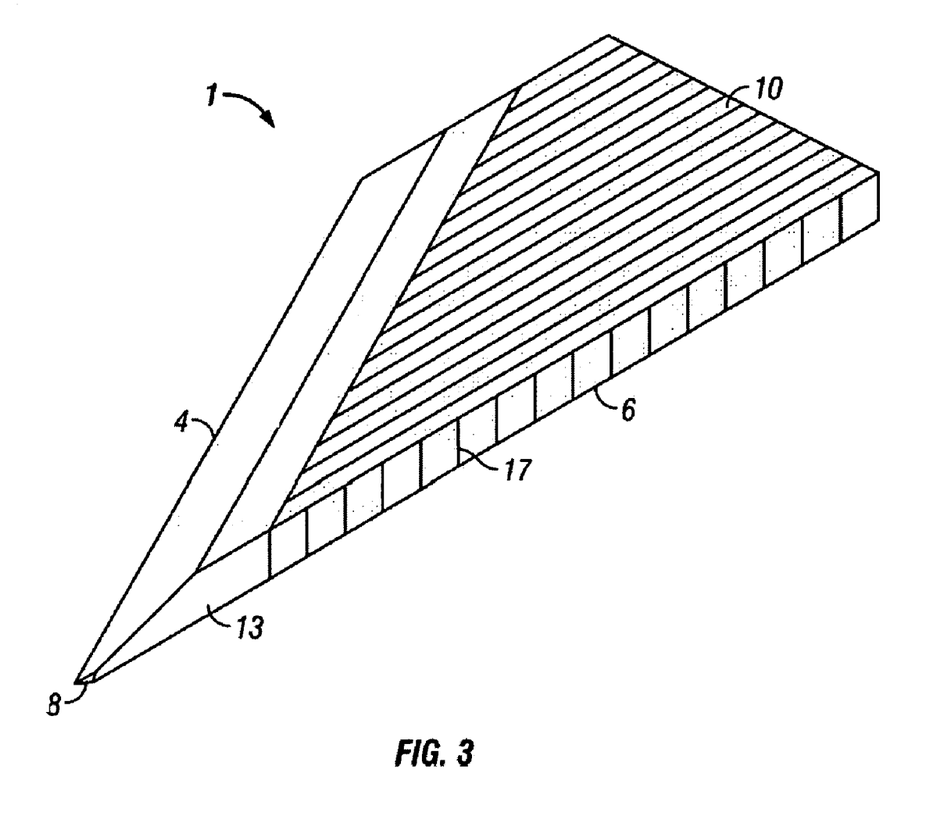
FIG. 3 illustrates the bifacet tip of FIG. 1A in a third embodiment.

In another configuration, as shown in FIG. 3, the tip 1 may be formed to include a facet 13 formed from diamond and a portion 17 formed from electrically conductive material, such as tungsten nitride, that is deposited onto the surface of the tip 1. In this configuration, the portion 17 may be used to deliver energy to the incision site. The tip 1, in FIG. 3, may optionally include the electrodes 10. In other configurations, the tip 1 may be formed from any combination of materials listed in Table 1 below. Thus, for example, the tip 1 could be formed from a conductive steel and also include a cutting edge 4 made from, for example, diamond. In this case, the cutting edge 4 could be bonded to a conductive steel portion 17 of the tip 1 by glue.

Figure 2B:
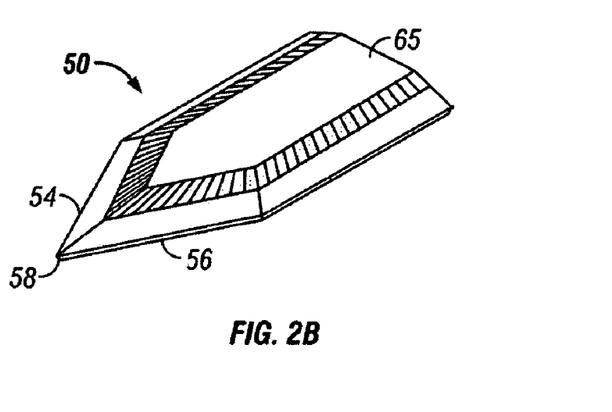
FIG. 2B illustrates the lance or spear tip of FIG. 1B in a second embodiment.

FIG. 1B illustrates a tip 50 similar to the tip 1. The tip 50, however, includes two beveled edges 54, 56 to form a lance or spear. The edges 54, 56 can be used to cut, and the apex 58 can be used to pierce. Similar to the tip 1, the tip 50 may include one or more electrodes 65 formed on both sides of the tip 50 such that the edges 54, 56 are exposed (FIG. 1B). Alternatively, the electrode 65 may be formed on only a portion of the tip 50 (FIG. 2B).

The edges 4, 54, 56 may have a sharpness of about 1 $\mu$m–25 nm. Table 1 below lists examples of various materials from which the tips 1, 50 can be formed.

The "hardness" value can be used to determine a material's resistance to wear. The "strength" value can be used to determine a material's resistance to fracture or plastic deformation. The "flexure strength" can be used to determine how easily the material can be sharpened. If the flexure strength is not sufficient, a material may bend or break during sharpening. The "specific heat" can be defined as heat capacity. Combining the specific heat and "thermal conductivity" values, it can determined how quickly a material may warm during a surgical procedure. The thermal conductivity value can be used to determine how quickly energy can pass to, for example, a heat sink coupled to the tips 1, 50. The specific heat value can be used to determine a temperature rise of the material, once a portion of the energy has passed to the heat sink.

Figure 4:
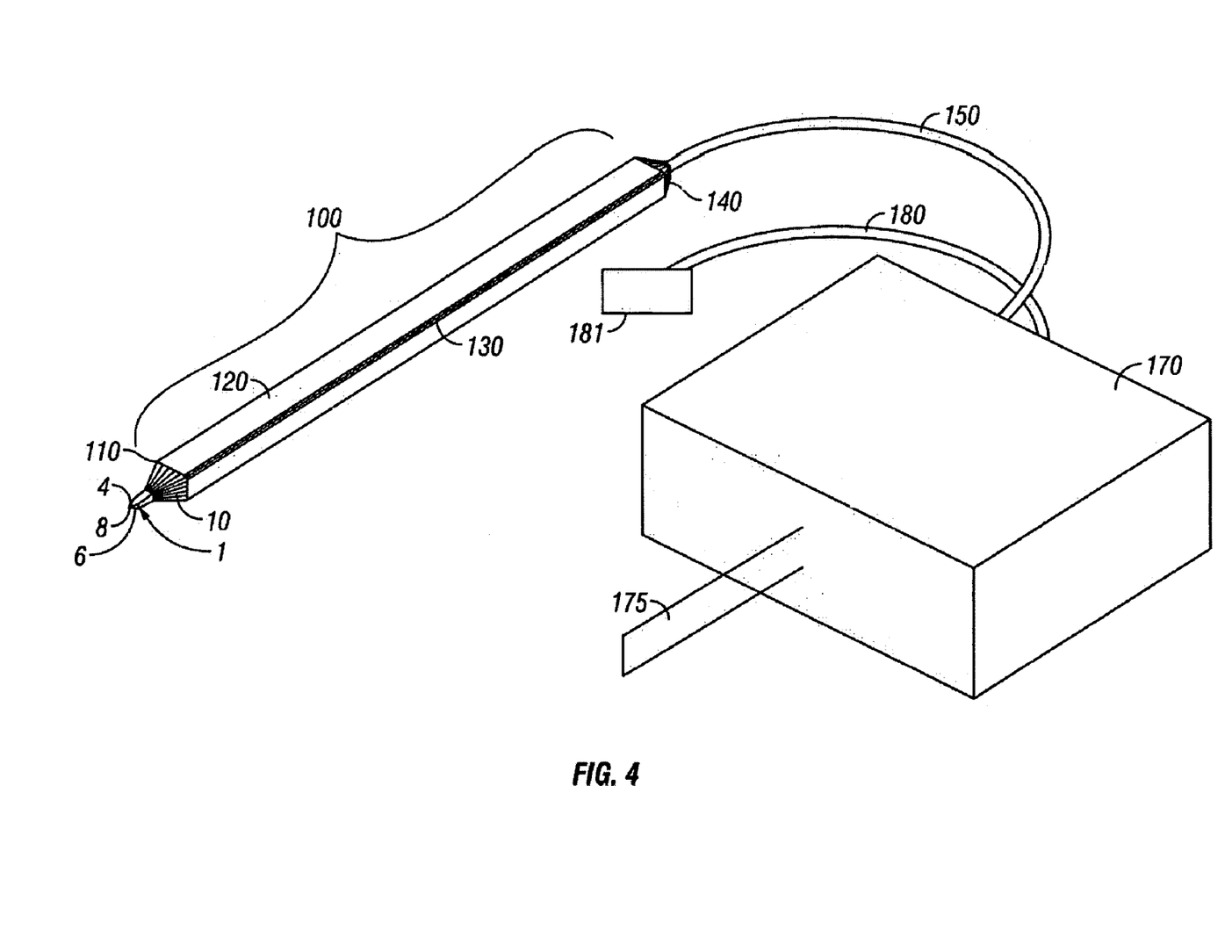
FIG. 4 illustrates a surgical tool coupled to an energy source in accordance with the present invention.

FIG. 4 diagrammatically illustrates an example of a cutting and cauterizing surgical tool 100. The surgical tool 100 includes a handle 120. For simplicity, the following discussion will assume that the tip 1 is coupled to the handle 120. However, the tip 50 or other similar tips can also be used.

Referring again to FIG. 4, the tip 1 is coupled to the distal end 110 of the handle 120. Passing through the handle 120 is a contact electrode 130. Preferably, the contact electrode 130 is configured to be in electrical contact with the electrodes 10 formed on the tip 1. In one configuration, the contact electrode 130 is formed from 300-series stainless steel that is passivated or gold plated.

In FIG. 4, the contact electrode 130 extends substantially from the distal end 120 to the proximal end 140 of the handle 120. Attached to the proximal end 140 of the contact electrode 130 is a cable 150. The cable 150 is preferably connected to an energy source 170. Suitable energy sources are, for example, a Bovie™ generator.

The source 170 may include a pedal 175 and a cable 180. The cable 180 may be coupled to a return electrode 181 situated on or under the patient's body. The switch 175 may be used by a surgeon to manually turn on and off the energy source 170. Alternatively, the source 170 may be activated automatically, for example, in predetermined time intervals.

In operation, the surgeon presses the switch 175. This activates the source 170. The source 170 then delivers an electrical current to the contact electrode 130 via the cable 150. The electrical current may be increased by, for example, repeatedly pressing the switch 175. Once the electrical current is passed to the contact electrode 130, the current then passes to the electrodes 10 on the tip 1. The current then passes through the patient's body to the cable 180 via the return electrode 181. This configuration thus forms a complete electrical circuit. In this way, the surgeon can use the non-cutting edges of the tip 1 to cauterize at the incision site. Additionally, a surgeon can also perform cutting procedures using the tip edge 4 and apex 8. The surgeon can thus use the same surgical tool to perform both cutting and cauterizing, without having to switch between separate surgical tools, as in known systems.

TABLE 1

| MATERIAL | HARDNESS Moh; Knoop (kg/mm$^2$) | THERMAL CONDUCTIVITY (W/cm · K) | SPECIFIC HEAT (J/g · K) | FLEXURE STRENGTH (MPa) |
| --- | --- | --- | --- | --- |
| diamond (11a) | 10; 7000–10,000 | 5–25 | 0.52 | 2940 |
| silicon carbide | 9.5; 2480–3500 | 4.5–4.9 | 0.67–0.69 | 250 |
| sapphire | 9; 1370–2250 | 0.23–0.46 | 0.75–0.78 | 1200 |
| tungsten carbide | 8.5–9.5; 1800–3000 | 0.63 | ~0.3 | ~2000 |
| steels | 5–8.5 | 0.14–0.85 | 0.45 | 800 |

During cutting procedures, electromagnetic radiation, for example, from a laser, may be delivered through the handle 120. The radiation may be delivered using a waveguide (not shown) or other similar device. The radiation may be emitted through the edge 4 and the face 6. For the tip 50, the radiation may be emitted through the edges 54, 56.

Figures 5A, 5B:
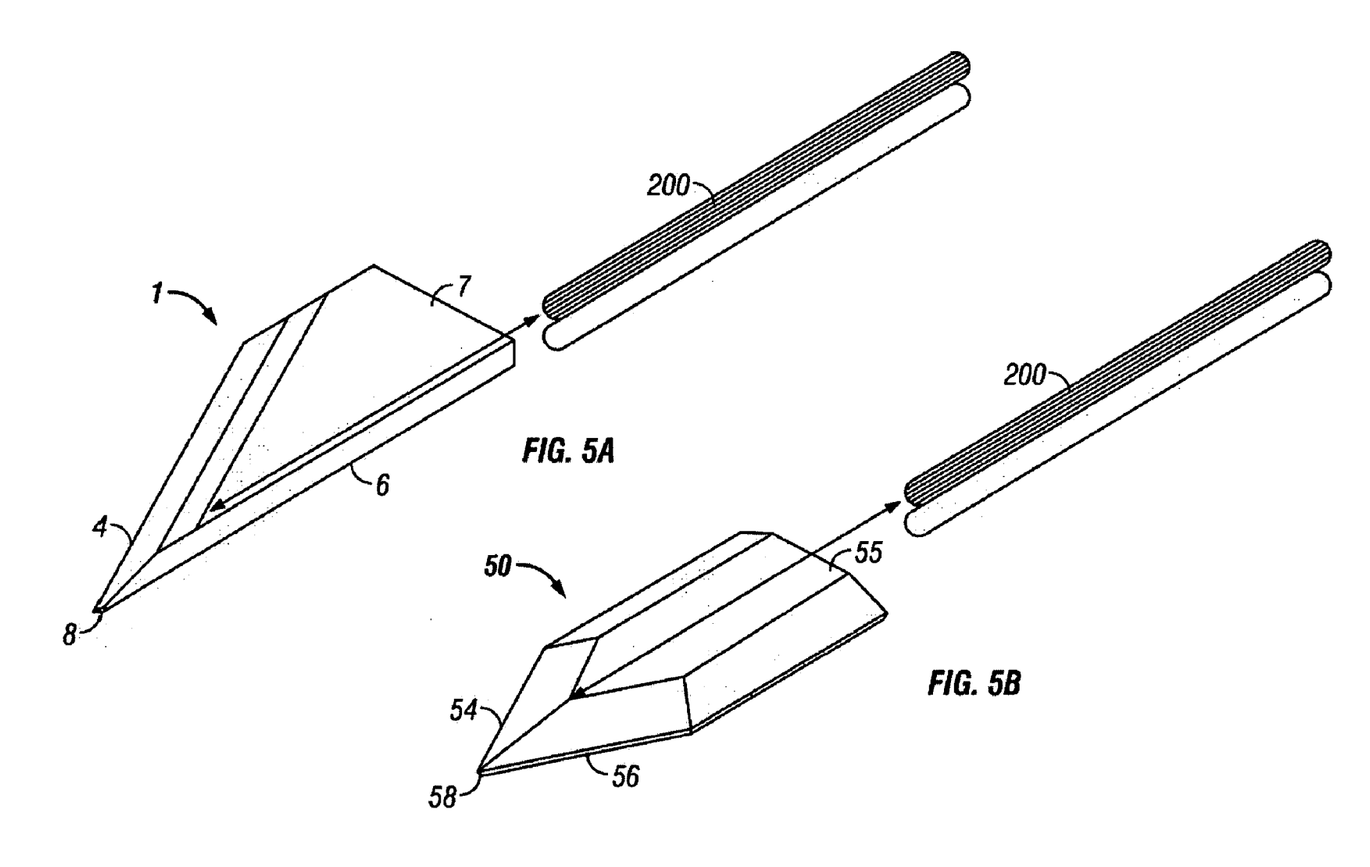
FIG. 5A illustrates the bifacet tip of FIG. 1A in a fourth embodiment.
FIG. 5B illustrates the lance or spear tip of FIG. 1B in a third embodiment.

FIG. 5A illustrates the tip 1 in a fourth embodiment. In FIG. 5A, an electrode 200 sides parallel to the face 6, and across a surface 7 of the tip 1. The electrodes 10, in this embodiment, may be optional. FIG. 5B shows the tip 50 in a third embodiment. In FIG. 5B, the conductor 200 slides across a surface 55 of the tip 50. The tip 50 may optionally include the electrodes 65.

Figure 8:
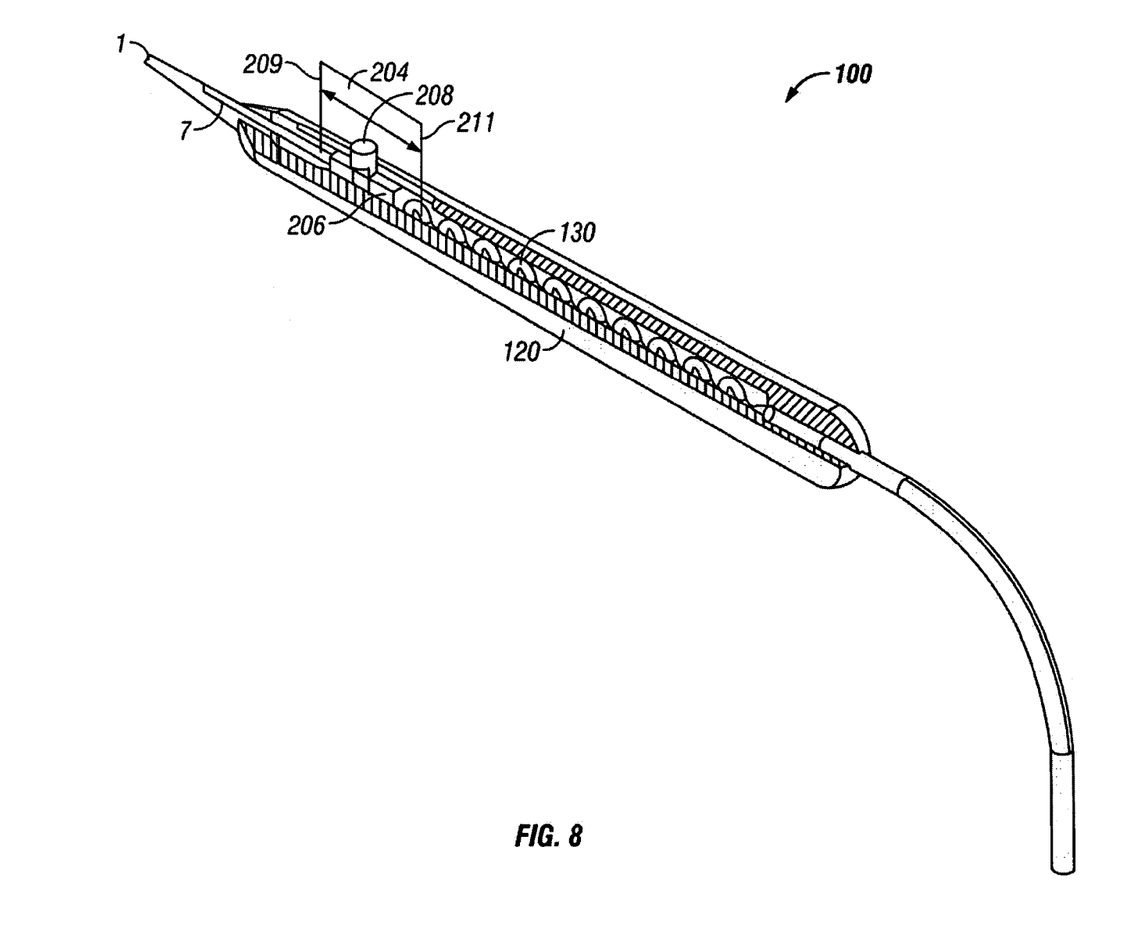
FIG. 8 illustrates the surgical tool of FIG. 4 having a push/pull device.

FIG. 8 shows an example of a push/pull device 204 for sliding the electrode. FIG. 8 shows the tip 1 coupled to the handle 120 with the integrated push/pull device 204. Alternatively, the tip 1 could be replaced with the tip 50 and also be used with the device 204. The device 204 includes a body 206 and a projection 208. The electrode 200 is coupled to a distal end 209 of the body 206. The contact electrode 130 is coupled to a proximal end 211 of the body 206. In this configuration, the contact electrode 130 and the electrode 200 are electrically coupled together inside the body 206, such that electrocautery energy can be delivered to the electrode 200.

In operation, a surgeon can move the electrode 200 to and from the application site using the projection 208. For example, a surgeon can manually push the projection 208 toward the tip 1. This causes the electrode 200 to travel toward the application site across the surface 7. Conversely, the surgeon can retract the electrode 200 by sliding the projection 208 in a direction away from the application site.

Figure 6:
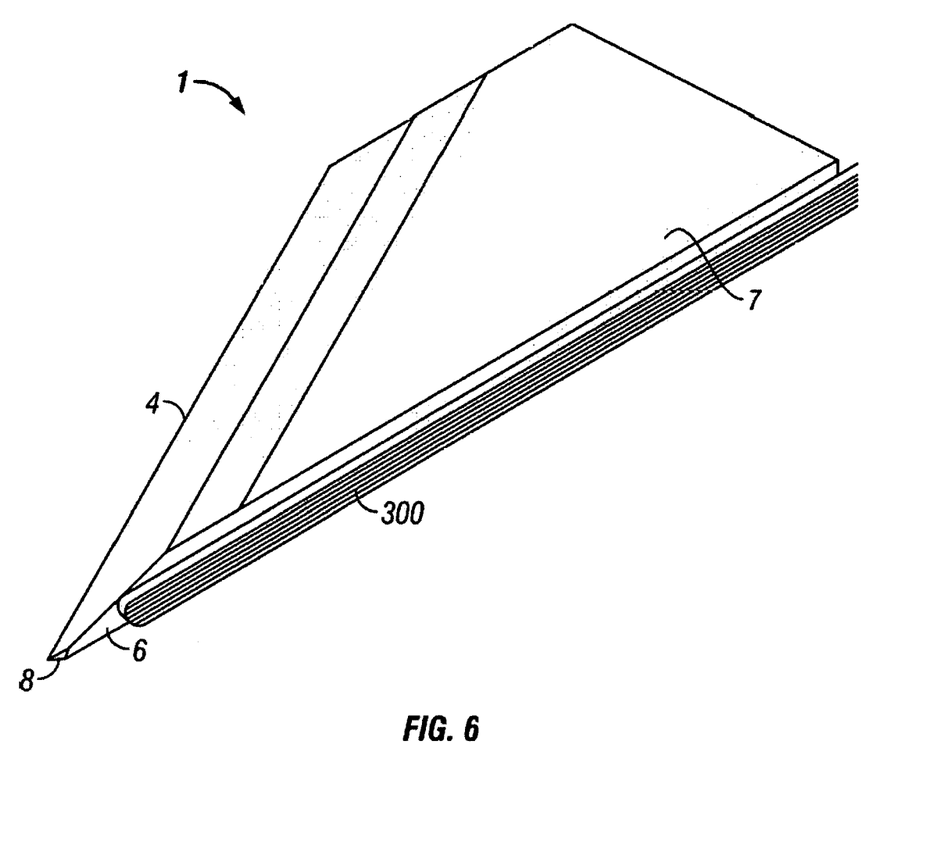
FIG. 6 illustrates the bifacet tip of FIG. 1A in a fifth embodiment.

FIG. 6 illustrates an electrode 300 bonded parallel to the face 6 on the surface 7. The electrode 300 may have a diameter of about 0.6 mm or less. The electrode 300 may be formed from materials similar to the electrodes 10. The electrode 300 forms an electrical contact with the contact electrode 130 similar to the electrodes 10. In this configuration, the electrodes 10 may be optional. The electrode 300 may be a wire electrode.

Figure 7:
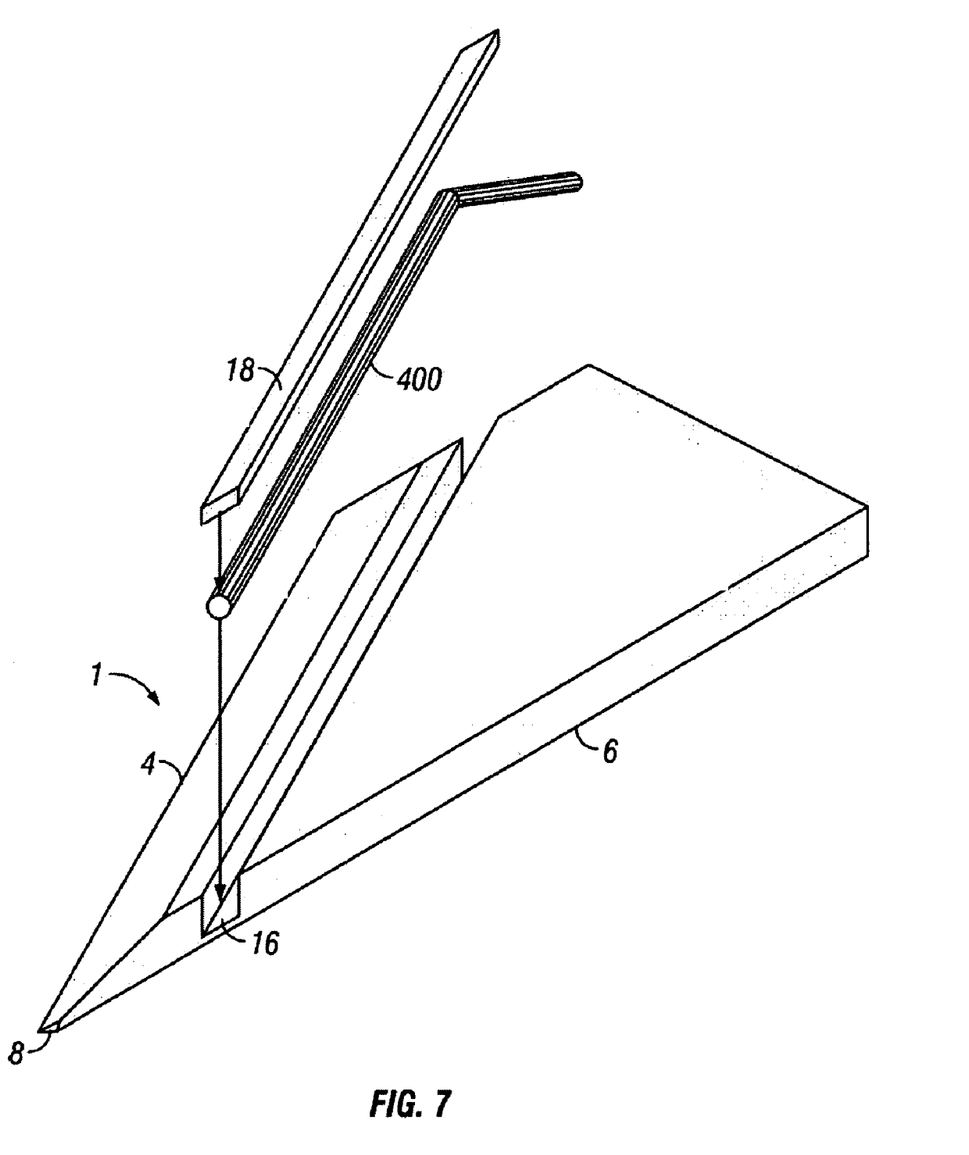
FIG. 7 illustrates the bifacet tip of FIG. 1A in a sixth embodiment.

FIG. 7 illustrates an electrode 400 formed integral with the tip 1. The electrode 400 is embedded in a cavity 16 of the tip 1. The electrode may be about 0.25 mm or less. An insulation layer 18 may cover at least a portion of the electrode 400. The electrode 400 may be a wire electrode. Similar to the electrode 300, the electrode 400 forms an electrical contact with the contact electrode 130. The cavity 16 may also be filled with suitable bonding or filling material to secure the electrode 400 inside the cavity 16.

Figure 9:
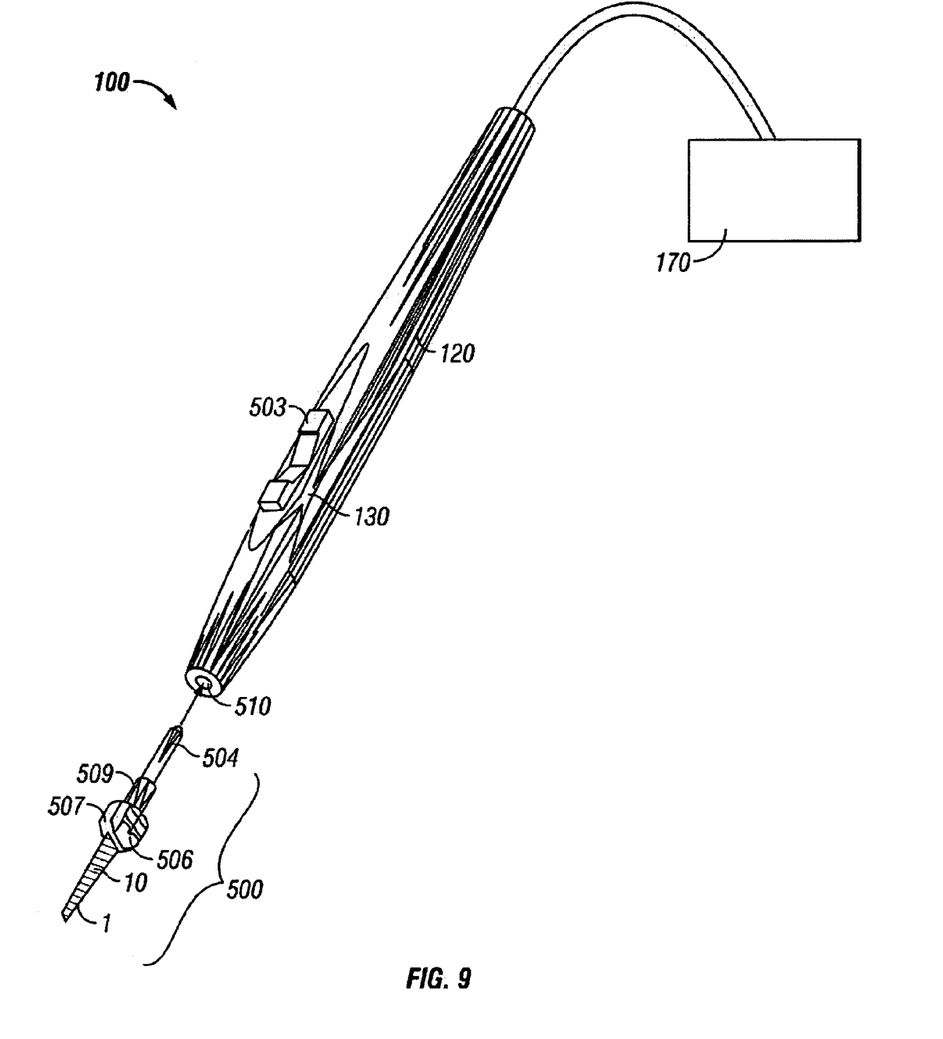
FIG. 9 illustrates the surgical tool of FIG. 4 having a removable device.

In another configuration, the surgical tool 100 may include a removable device 500. The device 500 includes the tip 1 rigidly attached to a plug 506. The plug 506 includes a locking clip 507 to secure the tip 1, and a pin 504 coupled to the locking clip 507 with a mount 509. The pin 504 is coupled to the tip 1 via the plug 506, such that the pin 504 is in electrical communication with the electrodes 10 on the tip 1. The pin 504 is configured to frictionally engage the handle 120 through an opening 510. When the pin 504 frictionally engages the handle 120, the pin 504 can electrically communicate with the electrode 130. As a result, electrical current from the source 170 can be delivered to the electrodes 10 via the electrode 130 and the pin 504.

Preferably, the surgical tool 100 (FIG. 9) also includes a button 503 formed integral with the handle 120. The button 503 is configured to allow a surgeon to deliver electrical current to the tip 1 via the electrode 130 by pressing the button 503. In this way, the surgeon can immediately and simply deliver electrical current to the application site to cauterize without having to use a separate electrocautery system. Further, the removable device 500 allows a surgeon to easily replace the tip 1 with a sharper or different tip.

The preferred configurations for the surgical tool 100 and the tips 1, 50 are inexpensive, simple, robust, and efficient. A surgeon can cut and cauterize using the same tool. Thus, separate surgical tools are not required, as in known systems. Further, the preferred surgical tools can be used for monopolar and bipolar electrocautery applications. This can be done by operating the electrodes 10, 65, 200, 300, and 400 at different potentials from the contact electrode 130. Additionally, the preferred surgical tool 100 is versatile. Depending on the application, the electrodes can optionally be formed on the tip, brazed to an edge of the tip, embedded in the tip, or retracted to and from the tip. Alternatively, the tip can be formed from a conductive member with a cutting edge bonded thereto. Further, the electrodes can be removed and replaced, by, for example, acid etching, such that the same tip can be used for multiple applications. A cooling mechanism may be coupled to the surgical tool to cool the tip during cutting or cauterizing.

A number of embodiments of the invention have been described. Nevertheless, it will be understood that various modifications may be made without departing from the spirit and scope of the invention. For example, a non-stick coating may be placed on at least a portion of the electrodes to minimize or prevent tissue from sticking to the tip. Suitable coatings include fluoropolymers, such as Teflon™, ceramic titanium alloys, and ceramics including transition metals, such as titanium nitride. Moreover, the electrodes 10, 65, 200, 300, and 400 may be removed from the tips 1, 50 by acid etching and can be coated with a friction reducing compound, such as Teflon™, Parylene™, or other compounds, which can prevent the adhesion of cauterized tissue to the cutting edges.

What is claimed is:

1. A surgical tool, comprising:
   a tip having at least one mechanical cutting edge; and
   at least one electrode attached to a non-mechanical cutting edge of the tip,
   wherein the at least one electrode comprises at least one wire rod, the wire rod having a thickness of about 0.6 mm or less.

2. A surgical tool, comprising:
   a tip having at least one mechanical cutting edge; and
   at least one electrode attached to a non-mechanical cutting edge of the tip,
   wherein the tip further comprises a cavity and wherein the at least one electrode comprises a wire rod embedded in the cavity.

3. A surgical tool, comprising:
   a tip having at least one mechanical cutting edge; and
   at least one electrode attached to a non-mechanical cutting edge of the tip,
   wherein the tip further comprises a cavity and wherein the at least one electrode comprises a wire rod embedded in the cavity,
   wherein the at least one electrode comprises a wire rod, the wire rod having a thickness of about 0.6 mm or less.

4. A device, comprising:
   a tip having at least one mechanical cutting edge;
   and at least one electrode attached to a non-mechanical cutting edge of the tip, wherein the at least one electrode itself delivers an electrical current to an application site to perform electrocautery at the application site, wherein the at least one electrode comprises a wire rod having a thickness of about 0.6 mm or less.

5. A device, comprising:
a tip having at least one mechanical cutting edge;
and at least one electrode attached to a non-mechanical cutting edge of the tip, wherein the at least one electrode itself delivers an electrical current to an application site to perform electrocautery at the application site,
wherein the tip comprises at least one cavity and wherein the at least one electrode comprises a wire rod embedded in the cavity.

6. A device, comprising:
a tip having at least one mechanical cutting edge;
and at least one electrode attached to a non-mechanical cutting edge of the tip, wherein the at least one electrode itself delivers an electrical current to an application site to perform electrocautery at the application site,
wherein the tip comprises at least one cavity and wherein the at least one electrode comprises a wire rod embedded in the cavity,
wherein the wire rod comprises a thickness of about 0.6 mm or less.

7. A system for cauterizing and cutting, comprising:
a surgical tool having a tip and a handle coupled to the tip, the tip including a mechanical cutting edge and at least one electrode attached to a non-mechanical cutting edge of the tip;
a contact electrode passing through the handle and electrically coupled to the at least one electrode; and
an energy source coupled to the handle to deliver electrocautery energy to the at least one electrode via the contact electrode,
wherein the at least one electrode comprises at least one wire rod, the wire rod having a thickness of about 0.6 mm or less.

8. A system for cauterizing and cutting, comprising:
a surgical tool having a tip and a handle coupled to the tip, the tip including a mechanical cutting edge and at least one electrode attached to a non-mechanical cutting edge of the tip;
a contact electrode passing through the handle and electrically coupled to the at least one electrode; and
an energy source coupled to the handle to deliver electrocautery energy to the at least one electrode via the contact electrode,
wherein the tip further comprises a cavity and wherein the at least one electrode comprises a wire rod embedded in the cavity.

9. A system for cauterizing and cutting, comprising:
a surgical tool having a tip and a handle coupled to the tip, the tip including a mechanical cutting edge and at least one electrode attached to a non-mechanical cutting edge of the tip;
a contact electrode passing through the handle and electrically coupled to the at least one electrode; and
an energy source coupled to the handle to deliver electrocautery energy to the at least one electrode via the contact electrode,
wherein the tip further comprises a cavity and wherein the at least one electrode comprises a wire rod embedded in the cavity,
wherein the at least one electrode comprises a wire rod, the wire rod having a thickness of about 0.6 mm or less.

10. A surgical tool, comprising:
a tip having at least one mechanical cutting edge and at least one electrode attached to a non-mechanical cutting edge of the tip, the tip being removably and frictionally engaged to a handle; and
a contact electrode formed inside the handle, the contact electrode being in electrical communication with the at least one electrode when the tip is removably and frictionally engaged to the handle,
wherein the at least one electrode comprises at least one wire rod, the wire rod having a thickness of about 0.6 mm or less.

11. A surgical tool, comprising:
a tip having at least one mechanical cutting edge and at least one electrode attached to a non-mechanical cutting edge of the tip, the tip being removably and frictionally engaged to a handle; and
a contact electrode formed inside the handle, the contact electrode being in electrical communication with the at least one electrode when the tip is removably and frictionally engaged to the handle;
wherein the tip further comprises a cavity and wherein the at least one electrode comprises a wire rod embedded in the cavity.

12. A surgical tool, comprising:
a tip having at least one mechanical cutting edge and at least one electrode attached to a non-mechanical cutting edge of the tip, the tip being removably and frictionally engaged to a handle; and
a contact electrode formed inside the handle, the contact electrode being in electrical communication with the at least one electrode when the tip is removably and frictionally engaged to the handle,
wherein the tip further comprises a cavity and wherein the at least one electrode comprises a wire rod embedded in the cavity,
wherein the at least one electrode comprises a wire rod, the wire rod having a thickness of about 0.6 mm or less.

13. A surgical tool, comprising:
a tip having at least one mechanical cutting edge, the edge not being formed from an electrode; and
at least one electrode attached to a non-mechanical cutting edge of the tip,
wherein the at least one electrode comprises at least one wire rod, the wire rod having a thickness of about 0.6 mm or less.

14. A surgical tool, comprising:
a tip having at least one mechanical cutting edge, the edge not being formed from an electrode; and
at least one electrode attached to a non-mechanical cutting edge of the tip,
wherein the tip further comprises a cavity and wherein the at least one electrode comprises a wire rod embedded in the cavity.

15. A surgical tool, comprising:
a tip having at least one mechanical cutting edge, the edge not being formed from an electrode; and
at least one electrode attached to a non-mechanical cutting edge of the tip,
wherein the tip further comprises a cavity and wherein the at least one electrode comprises a wire rod embedded in the cavity,
wherein the at least one electrode comprises a wire rod, the wire rod having a thickness of about 0.6 mm or less.

* * * * *